United States Patent [19]
Gan et al.

[11] Patent Number: 5,962,720
[45] Date of Patent: Oct. 5, 1999

[54] METHOD OF SYNTHESIZING UNSYMMETRIC ORGANIC CARBONATES AND PREPARING NONAQUEOUS ELECTROLYTES FOR ALKALI ION ELECTROCHEMICAL CELLS

[75] Inventors: Hong Gan, East Amherst; Marcus Palazzo, Niagara Falls; Esther S. Takeuchi, East Amherst, all of N.Y.

[73] Assignee: Wilson Greatbatch Ltd., Clarence, N.Y.

[21] Appl. No.: 08/865,236

[22] Filed: May 29, 1997

[51] Int. Cl.$^6$ ..................................................... C07C 68/06
[52] U.S. Cl. ........................... 558/277; 558/270; 558/274
[58] Field of Search .................... 558/270, 274, 558/277

[56] References Cited

U.S. PATENT DOCUMENTS

| | | | |
|---|---|---|---|
| 4,652,667 | 3/1987 | Green | 558/277 |
| 5,206,408 | 4/1993 | Liotta | 558/277 |
| 5,210,268 | 5/1993 | Fukuoka et al. | 558/270 |
| 5,322,958 | 6/1994 | Dreoni et al. | 558/277 |
| 5,443,928 | 8/1995 | Takeuchi et al. | 429/218 |
| 5,484,669 | 1/1996 | Okuno et al. | 429/194 |
| 5,521,027 | 5/1996 | Okuno et al. | 429/194 |
| 5,760,273 | 6/1998 | Inaba et al. | 558/277 |

FOREIGN PATENT DOCUMENTS

| | | |
|---|---|---|
| 0622862 | 11/1994 | European Pat. Off. . |
| 2148665 | 6/1990 | Japan . |
| 5299118 | 11/1993 | Japan . |
| 6166660 | 6/1994 | Japan . |
| 6290809 | 10/1994 | Japan . |
| 7-010811 | 1/1995 | Japan . |
| 7288140 | 10/1995 | Japan . |
| 7296848 | 11/1995 | Japan . |

OTHER PUBLICATIONS

Edmund P. Woo and Frank C.W. Cheng, J. Org. Chem. 1986, 51, 3704–3706; Carbonylation in Strong Acid. Lactones From Allylic Derivatives.

Ichiro Minami and Jiro Tsuji, Tetrahedron 1987, 43, 3903–3915; Dehydrogenation of Alochols With Allyl Carbonates Catalyzed By Palladium or Ruthenium Complexes.

Database CAPLUS on STN®, Chemical Abstracts Service, (Columbus, Ohio), Accession No. 1995:441438; JP 07–010811, abstract, 1995.

Abstract of JP 07–10811 A (Hasegawa et al.); Japanese Patent Office, 1995.

Derwent Abstract No. 1995–085371; Derwent Information Ltd., 1995; Hasegawa et al., JP 07–10811 A.

*Primary Examiner*—Michael G. Ambrose
*Attorney, Agent, or Firm*—Hodgson, Russ, Andrews, Woods & Goodyear LLP

[57] ABSTRACT

The present invention relates to an improved method of synthesizing unsymmetric linear organic carbonates comprising the reaction of two symmetric dialkyl carbonates, $R^1$ and $R^2$, in the presence of a nucleophilic reagent or an election donating reductant as a catalyst, wherein $R^1$ and $R^2$ can be either saturated or unsaturated alkyl or aryl groups, is described. The present invention further provides a preparation method for a nonaqueous organic electrolyte having an unsymmetric linear organic carbonate as a co-solvent.

26 Claims, No Drawings

METHOD OF SYNTHESIZING UNSYMMETRIC ORGANIC CARBONATES AND PREPARING NONAQUEOUS ELECTROLYTES FOR ALKALI ION ELECTROCHEMICAL CELLS

BACKGROUND OF INVENTION

1. Field of the Invention

The present invention generally relates to the conversion of chemical energy to electrical energy, and more particularly, to a nonaqueous electrolyte for alkali metal electrochemical cells. A preferred form of the present invention relates to an electrolyte for rechargeable alkali metal electrochemical cells such as rechargeable lithium ion cells.

2. Prior Art

The choice of electrolyte solvent is one of the most important factors in determining cell discharge performance characteristics. For rechargeable lithium ion cells, sometimes referred to as "rocking chair" cells, nonaqueous organic electrolytes containing carbonate solvents, for example propylene carbonate (PC), ethylene carbonate (EC), dimethyl carbonate (DMC) and diethyl carbonate (DEC) are generally used because of their high oxidative stability toward cathode active materials and their high kinetic stability toward the alkali metal anode. The latter characteristic is believed to be caused by anode surface passivation.

Recently, it has been demonstrated that the utilization of an unsymmetric linear carbonate, such as ethyl methyl carbonate (EMC), as a co-solvent in a nonaqueous electrolyte in many cases provides improved cell discharge characteristics including increased energy density, increased discharge capacity, longer cycle life and higher safety performance in comparison to the conventional solvents discussed above. This has been reported in the literature including published European Patent Application No. 0622862A1; U.S. Pat. Nos. 5,484,669 to Okuno et al. and 5,521,027 Okuno et al.; and Japanese Laid-Open Patent Publication Nos. 2-148665, 6-290809, 5-299118, 7-296848, 7-288140. Although unsymmetric linear carbonates have been demonstrated to be acceptable co-solvents for nonaqueous electrolytes activating rechargeable alkali metal ion cells, the availability and the relatively high price of these solvents has limited their wide spread application.

A well known method for synthesizing an unsymmetric carbonate is the esterification of alkyl chloroformate with alcohol under base (pyridine or amine) catalysis, as shown in equation 1. This synthesis is reported in the literature including: Edmund P. Woo and Frank C. W. Cheng, *J. Org. Chem.* 1986, 51, 3704–3706; and Ichiro Minami and Jiro Tsuji, Tetrahedron 1987, 43, 3903–3915.

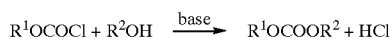
(1)

The esterification reaction of equation 1 requires very reactive and highly toxic starting materials that necessitate strictly controlled reaction conditions. Consequently, that esterification reaction is not a desirable synthetic route for large scale production of unsymmetric carbonates.

Another method for unsymmetric linear carbonate synthesis is disclosed in Japanese Laid-Open Patent Publication No. 6-166660, which reports an ester exchange reaction of a dialkyl carbonate with alcohol under a weak base (metal ion carbonate salt) catalysis, as shown in equation 2.

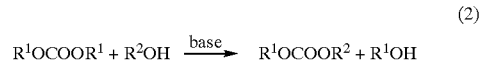
(2)

The reaction in equation 2 proceeds under fairly mild conditions. The starting materials are less toxic than those disclosed in equation 1 and are relatively easy to handle. However, the disadvantage of an ester exchange reaction of a dialkyl carbonate with alcohol under base catalysis is that the synthesis products include a mixture of three dialkyl carbonates and two alcohols. For instance, when a 1:1 molar ratio of DMC and ethanol is used as the starting materials, the product mixture contains a 46:44:10 molar ratio of DMC:EMC:DEC and the relative ratio of methanol and ethanol, theoretically, is 64:34. The molar ratio of the desired EMC product is, thus, only about 22% of the resulting mixture. Since alcohol is an undesirable impurity in any electrolyte intended to activate an alkali metal cell and in particular lithium primary cells and lithium ion rechargeable cells, vigorous purification of the carbonate products to remove the undesired alcohols is needed. Sometimes, this goal is very difficult to achieve due to the similar boiling points of the reaction mixture components.

According to the present invention, the above discussed problems and difficulties of the prior art preparation techniques are overcome by synthesizing unsymmetric carbonates using a new methodology. Increased product yield and an alcohol free solvent are obtained according to the present invention. In addition, the reaction product mixture of the present invention can also be used directly as a battery electrolyte solvent or co-solvent without further purification

SUMMARY OF THE INVENTION

The present invention relates to an improved method of synthesizing unsymmetric linear organic carbonates. The improved method comprises the reaction of two symmetric dialkyl carbonates, $R^1OCOOR^1$ and $R^2OCOOR^2$, in the presence of a nucleophilic reagent and/or an electron donating reductant as a catalyst, wherein $R^1$ and $R^2$ can be either saturated or unsaturated alkyl or aryl groups. A further object of the present invention is to provide a preparation method for a nonaqueous organic electrolyte having an unsymmetric linear organic carbonate as a co-solvent.

DETAILED DESCRIPTION OF THE INVENTION

According to the present invention, an unsymmetric linear carbonate is synthesized via an ester exchange reaction from two symmetric dialkyl carbonate reactants in the presence of a catalyst. As shown in equation 3, the two symmetric dialkyl carbonates, $R^1$ and $R^2$, are reacted in the presence of a nucleophilic reagent or an election donating reductant as a catalyst, where $R^1$ and $R^2$ can be either saturated or unsaturated alkyl or aryl groups. The two symmetric dialkyl carbonates are preferably present in the starting reaction mixture in a molar ration of about 9:1 to 1:9.

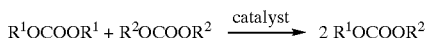

$$R^1OCOOR^1 + R^2OCOOR^2 \xrightarrow{\text{catalyst}} 2\, R^1OCOOR^2 \quad (3)$$

The reaction mechanism of the ester exchange reaction of the present invention is believed to proceed according to the following reaction equations:

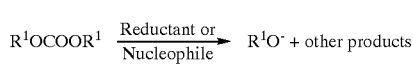

$$R^1OCOOR^1 \xrightarrow{\text{Reductant or Nucleophile}} R^1O^- + \text{other products} \quad (4)$$

$$R^2OCOOR^2 + R^1O^- \longrightarrow R^2OCOOR^1 + R^2O^- \quad (5)$$

$$R^1OCOOR^1 + R^2O^- \longrightarrow R^2OCOOR^1 + R^1O^- \quad (6)$$

Equation 4 illustrates an initiation step in the ester exchange reaction of the present invention where the intermediate alkoxide anion is generated. The alkoxide anion then reacts with one of the starting carbonates to generate the desired unsymmetric carbonate and a second alkoxide intermediate. The second alkoxide intermediate reacts with another starting carbonate to form the desired unsymmetric carbonate and to regenerate the first alkoxide intermediate. The reaction will proceed until reaching equilibrium.

Two types of catalysts are able to initiate the ester exchange reaction of the present invention, namely, a nucleophilic reagent such as an alkoxide and an amide, an organic alkyl or aryl anion and an electron donating reductant including an alkali metal such as lithium, an alkalated carbon such as lithiated carbon and a samarium(II) salt such as samarium(II) diiodide. Suitable nucleophilic reagents include lithium dialkylamide, lithium alkoxide, an alkyl lithium and an aryl lithium. Some useful catalysts are considered to be both nucleophilic and reductant such as lithium cyclopentadienylide and calcium hydride.

Thus, in the presence of the catalyst, a reaction mixture containing three carbonates is obtained. The relative molar ratio between the product carbonates, however, is dependent upon the initial ratio of the starting carbonates. Up to a 50% yield of the product unsymmetric carbonate is achieved if the initial ratio of the two symmetric dialkyl carbonate reactants is 1:1. Such a reaction yield is more than double that obtained from the prior art esterification of a dialkyl carbonate with alcohol under a weak base catalysis, as reported in the previously discussed Japanese Laid-Open Patent Publication No. 6-166660.

In the present synthesis, the catalyst is easily separated from the reaction mixture by filtration through a column of Alumina or Silica Gel. After removing the catalyst, the product is readily purified by utilizing commonly known separation techniques, such as vacuum distillation, normal pressure distillation, high pressure distillation, extraction, crystallization, chromatography and the like. Furthermore, the starting materials are recyclable after product separation.

One additional advantage of the ester exchange reaction of the present invention is that the reaction does not yield undesirable side products under properly controlled reaction conditions. Often, all three carbonates in the product mixture are utilized in the nonaqueous electrolyte activating lithium ion batteries. The step of separating three product carbonates may or may not be necessary. Therefore, the ratio of the three carbonates can be controlled by changing the initial ratio of the starting materials or by adding starting materials to the final reaction product mixture. For example, if DMC and DEC are used as starting materials, the ratio of EMC in the final reaction mixture can range from about 41% to 48% for starting ratios of DMC:DEC of about 4:2 to 2:4, respectively. Another preferred unsymmetric carbonate is methyl propyl carbonate formed from the esterification reaction of dimethyl carbonate and dipropyl carbonate according to the present invention.

The nonaqueous electrolyte containing as a co-solvent an unsymmetrical linear carbonate synthesized according to the present methods is useful in activating many types of secondary, lithium-ion cells and batteries. Such electrochemical systems can comprise, for example, a carbonaceous anode and a lithium-retentive cathode. The carbon anode comprises any of the various forms of carbon (e.g., coke, graphite, acetylene black, carbon black, etc.) which are capable of reversibly retaining the lithium species. Graphite is preferred due to its relatively high lithium-retention capacity Carbon fibers are particularly advantageous because they have excellent mechanical properties which permit them to be fabricated into rigid electrodes that are capable of withstanding degradation during repeated charge discharge cycling. Moreover, their high surface area allows rapid charge/discharge rates. The carbon may be contacted to a conductive substrate such as by pressing, bonding and the like. A preferred carbonaceous material for the anode of a secondary electrochemical cell is described in U.S. Pat. No. 5,443,928 to Takeuchi et al., which is assigned to the assignee of the present invention and incorporated herein by reference.

A typical graphite anode is fabricated by mixing about 90 to 99 weight percent graphite with 1 to 10 weight percent of a powdered fluoro-resin binder This mixture is rolled onto a current collector such as nickel, stainless steel, or copper foil or screen. The graphite electrode can be lithiated electrochemically using a lithium electrode or chemically. The $Li_xC_6$ electrode can have an x range between 0.1 and 1.0.

The cathode comprises a lithiated material that is stable in air and readily handled. Examples of such air-stable lithiated cathode materials include oxides, sulfides, selenides, and tellurides of such metals as vanadium, titanium, chromium, copper, molybdenum, niobium, iron, nickel, cobalt and manganese. The more preferred oxides include $LiNiO_2$, $LiMn_2O_4$, $LiCoO_2$, $LiCo_{0.92}Sn_{0.08}O_2$ and $LiCo_{1-x}Ni_xO_2$.

A typical cathode for a rechargeable secondary cell is made from a mixture of 80 to 95 weight percent cathode active material, 1 to 10 weight percent of a conductive diluent and 1 to 10 weight percent of a binder material. Suitable conductive diluents include acetylene black, carbon black and/or graphite. Metal powders such as nickel, aluminum, titanium and stainless steel in powder form are also useful as conductive diluents when mixed with the above listed active materials. Fluoro-resin powders such as powdered polytetrafluoroethylene (PTFE) or powdered polyvinylidene fluoride (PVDF) are preferred for the binder of both the anode and the cathode.

The cell of the present invention includes a separator to provide physical separation between the anode and cathode active electrodes. The separator is of electrically insulative material to prevent an internal electrical short circuit between the electrodes, and the separator material also is chemically unreactive with the anode and cathode active materials and both chemically unreactive with and insoluble in the electrolyte. In addition, the separator material has a degree of porosity sufficient to allow flow therethrough of the electrolyte during the electrochemical reaction of the cell. The form of the separator typically is a sheet which is placed between the anode and cathode electrodes. Such is the case when the anode is folded in a serpentine-like structure with a plurality of cathode plates disposed intermediate the anode folds and received in a cell casing or when the electrode combination is rolled or otherwise formed into a cylindrical "jellyroll" configuration.

The unsymmetric linear carbonate synthesized according to the methods of the present invention serve either as a co-solvent or as a single solvent in a nonaqueous, tonically conductive electrolyte operatively associated with the anode and the cathode electrodes. The electrolyte serves as a medium for migration of ions between the anode and the cathode during the electrochemical reactions of the cell, and nonaqueous solvents in addition to the unsymmetric linear carbonate are chosen so as to exhibit those physical properties necessary for ionic transport, namely, low viscosity, low surface tension and wettability.

Suitable nonaqueous electrolytes are comprised of an inorganic salt dissolved in a nonaqueous solvent and more preferably an alkali metal salt dissolved in a mixture of aprotic organic solvents comprising a low viscosity solvent including organic esters, ethers and dialkyl carbonates, and mixtures thereof, and a high permittivity solvent including cyclic carbonates, cyclic esters and cyclic amides, and mixtures thereof. Suitable nonaqueous solvents are substantially inert to the anode and cathode electrode materials and preferred low viscosity solvents include tetrahydrofuran (THF), methyl acetate (MA), diglyme, triglyme, tetraglyme, dimethyl carbonate (DMC), diethyl carbonate (DEC), dipropyl carbonate (DPC), methyl ethyl carbonate (MEC), methyl propyl carbonate (MPC), ethyl propyl carbonate (EPC), 1,2-dimethoxyethane (DME), and others. Preferred high permittivity solvents include propylene carbonate (PC), ethylene carbonate (EC), butylene carbonate (BC), acetonitrile, dimethyl sulfoxide, dimethyl formamide, dimethyl acetamide, γ-butyrolactone (GBL) and N-methylpyrrolidinone (NMP) and others.

Known lithium salts that are useful as a vehicle for transport of alkali metal ions from the anode to the cathode, and back again include $LiPF_6$, $LiBF_4$, $LiAsF_6$, $LiSbF_6$, $LiClO_4$, $LiAlCl_4$, $LiGaCl_4$, $LiC(SO_2CF_3)_3$, $LiN(SO_2CF_3)_2$, LiSCN, $LiO_3SCF_2CF_3$, $LiC_6F_5SO_3$, $LiO_2CCF_3$, $LiSO_3F$, $LiB(C_6H_5)_4$ and $LiCF_3SO_3$, and mixtures thereof. Suitable salt concentrations typically range between about 0.8 to 1.5 molar, and a preferred electrolyte for a rechargeable lithium ion cell according to the present invention includes $LiAsF_6$ or $LiPF_6$ dissolved in a mixture of an unsymmetric organic carbonate such as ethyl methyl carbonate synthesized according to the present invention, ethylene carbonate and dimethyl carbonate.

The rechargeable cell of the present invention is initially in a discharged state and the lithium metal comprising the cathode is intercalated into the anode by applying an externally generated electrical potential to recharge the cell. The applied recharging electrical potential serves to draw the alkali metal from the cathode material, through the electrolyte and into the carbonaceous anode to saturate the carbon comprising the anode. The cell is then provided with an electrical potential and is discharged in a normal manner.

The assembly of the cell described herein is preferably in the form of a wound element cell. That is, the fabricated cathode, anode and separator are wound together in a "jellyroll" type configuration or "wound element cell stack" such that the anode is on the outside of the roll to make electrical contact with the cell case in a case-negative configuration. Using suitable top and bottom insulators, the wound cell stack is inserted into a metallic case of a suitable size dimension. The metallic case may comprise materials such as stainless steel, mild steel, nickel-plated mild steel, titanium or aluminum, but not limited thereto, so long as the metallic material is compatible for use with components of the cell.

The cell header comprises a metallic disc-shaped body with a first hole to accommodate a glass-to-metal seal/ terminal pin feedthrough and a second hole for electrolyte filling. The glass used is of a corrosion resistant type having up to about 50% by weight silicon such as CABAL 12, TA 23, FUSITE 425 or FUSITE 435. The positive terminal pin feedthrough preferably comprises molybdenum although titanium, aluminum, nickel alloy, or stainless steel can also be used. The cell header comprises elements having compatibility with the other components of the electrochemical cell and is resistant to corrosion. The cathode lead is welded to the positive terminal pin in the glass-to-metal seal and the header is welded to the case containing the electrode stack. The cell is thereafter filled with the electrolyte solution described hereinabove including at least one unsymmetric organic carbonate synthesized according to the present invention, and hermetically sealed such as by close-welding a stainless steel ball over the fill hole, but not limited thereto. This above assembly describes a case-negative cell which is the preferred construction of the exemplary secondary cell of the present invention. As is well known to those skilled in the art, the exemplary electrochemical system of the present invention can also be constructed in a case-positive configuration.

The following examples describe the manner and process of synthesizing an unsymmetric organic carbonate according to the present invention, and set forth the best mode contemplated by the inventors of carrying out the invention, but are not construed as limiting.

EXAMPLE I

A piece of lithium metal was added to a 1 to 1 molar ratio mixture of DMC (3.5 ml, 0.04 mol) and DEC (5.0 ml, 0.04 mol) in a flask under dry air in a dry room. The solution was stirred at room temperature for 3 days. The lithium metal broke up upon stirring. Gas chromatography (GC) analysis indicated that EMC was the only new product. The ratio of DMC:EMC:DEC was determined to be 1:0.6:1.

The results of this example demonstrate that the ester exchange reaction of the present invention can be catalyzed by a alkali metal, a strong reducing agent.

EXAMPLE II

A piece of lithiated carbon (gold color solid) was added to a 1 to 1 molar ratio mixture of DMC (3.5 ml, 0.04 mol) and DEC (5.0 ml, 0.04 mol) in a flask under dry air in a dry room. The solution was stirred at room temperature for 4 days. The color of the lithiated carbon turned from gold to black upon stirring. Gas chromatography analysis indicated that EMC was the only new product. The ratio of DMC:EMC:DEC was determined to be 1:1.3:1.2.

The results of this example demonstrate that the ester exchange reaction of the present invention can be catalyzed by lithiated carbon, also a strong reducing agent with oxidation potential around 0.1 V vs. lithium

EXAMPLE III 0.235 g of $SmI_2$ was added to a 1 to 1 molar ratio mixture of DMC (4.9 ml, 0.058 mol) and DEC (7.0 ml, 0.058 mol)

in a flask under Argon in a glove box. The resulting blue solution was stirred at room temperature for 9 days. Gas chromatography analysis indicated that EMC was present. The ratio of DMC:EMC:DEC was determined to be 1:2.2:1.5.

The results of this example demonstrate that the ester exchange reaction of the present invention can be catalyzed by $SmI_2$, a strong reducing agent with oxidation potential around 1.4 V to 1.5 V vs. lithium. The results suggest that any reducing reagent having oxidation potential below the reduction potential of the starting dialkyl carbonates will be able to catalyze ester exchange reactions according to the present invention.

EXAMPLE IV 0.021 g of $CaH_2$ was added to a 1 to 1 molar ratio mixture of DMC (4.9 ml, 0.058 mol) and DEC (7.0 ml, 0.058 mol) in a flask under dry air in a dry room The catalyst was not soluble in the solution. The resulting mixture was stirred at room temperature for 9 days. Gas chromatography analysis indicated that EMC was the only new product. The ratio of DMC:EMC:DEC was determined to be 1:2.4:1.5.

The results from this example demonstrate that the ester exchange reaction of the present invention can be catalyzed by a metal hydride, a strong reducing agent and a good hydride donor.

EXAMPLE V 0.021 g of lithium cyclopentadienylide was added to a 1 to 1 molar ratio mixture of DMC (4.9 ml, 0.058 mol) and DEC (7.0 ml, 0.058 mol) in a flask under Argon in a glove box. The catalyst was partially soluble to afford a yellow solution. The reaction mixture was stirred at room temperature for 6 days. Gas chromatography analysis indicated that EMC was present. The ratio of DMC:EMC:DEC was determined to be 1:2:1.

The results from this example demonstrate that the ester exchange reaction of the present invention can be catalyzed by lithium cyclopentadienylide, an organic anion lithium salt complex with oxidation potential estimated to be around 1.6 V vs. lithium. The organic anion can also act as a nucleophile.

EXAMPLE VI 0.0296 g of lithium diethylamide was added to a 1 to 1 molar ratio mixture of DMC (4.9 ml, 0.058 mol) and DEC (7.0 ml, 0.058 mol) in a flask under Argon in a glove box. The solution was stirred at room temperature for 2 days. Gas chromatography analysis indicated that EMC was present. The ratio of DMC:EMC:DEC was determined to be 1:2:1.

The results from this example demonstrate that the ester exchange reaction of the present invention can be catalyzed by lithium dialkylamide, a strong nucleophile.

EXAMPLE VII 0.0206 g of lithium methoxide was added to a 1 to 1 molar ratio mixture of DMC (4.9 ml, 0.058 mol) and DEC (7.0 ml, 0.058 mol) in a flask under Argon in a glove box. The catalyst was partially soluble in the solution. The reaction mixture was stirred at room temperature for 10 days. Gas chromatography analysis indicated that EMC was the only new product. The ratio of DMC:EMC:DEC was determined to be 1:2:1.

The results from this example demonstrate that the ester exchange reaction of the present invention can be catalyzed by lithium alkoxide, a strong nucleophile.

EXAMPLE VIII

A piece of lithium metal was added to a 1 to 1 molar ratio mixture of DMC (5.0 ml, 0.059 mol) and DPC (dipropyl carbonate 9.2 ml, 0.059 mol) in a flask under dry air in a dry room. The solution was stirred at room temperature for 5 days. Lithium metal broke up upon stirring. Gas chromatography analysis indicated that MPC was present. The ratio of DMC:MPC:DPC was determined to be 1:0.84:1.2.

The results from this example demonstrate that the ester exchange reaction of the present invention can also be achieved with a higher molecular weight dialkyl carbonate. Therefore, the reaction of the present invention is universal.

EXAMPLE IX

Mixtures of DMC and DEC in different starting molar ratios cording to Table 1 were stirred at room temperature under an gon filled glove box in the presence of lithium methoxide. ter 10 days, the reactions reached equilibrium. The molar tio of carbonates in the reaction mixture is listed in Table 1.

TABLE 1

Control of Carbonates Ratio

| Starting Ratio DMC:DEC | DMC (ml) | DEC (ml) | Lithium Methoxide (g) | Product Ratio MC:EMC:DEC |
|---|---|---|---|---|
| 4:2 | 5.6 | 4.0 | 0.016 | 46:41:13 |
| 3:2 | 5.1 | 4.8 | 0.016 | 35:48:17 |
| 2:2 | 4.9 | 7.0 | 0.022 | 24:48:28 |
| 2:3 | 3.4 | 7.3 | 0.018 | 15:46:39 |
| 2:4 | 2.8 | 8.1 | 0.018 | 11:42:47 |

This example illustrates that the ratio of the final three carbonate mixtures can be controlled by varying the initial starting carbonate molar ratio.

In Examples III, V, VI, VII and IX, gas chromatography analysis indicated that trace amounts of alcohols were present. The alcohol was believed to have been introduced by the reaction of the alkoxide anion with traces of water originally present in either the starting solvents or the surrounding atmosphere. If the reaction solution is kept dry, the trace amounts of alcohols are eliminated. In Examples I, II, IV and VIII, gas chromatography analysis indicated that no alcohols were present in the resulting carbonate mixture. This means that an alcohol free carbonate solvent mixture can be obtained without further purification under the choice of a proper catalyst and drying reagent.

In all examples, the reaction products were analyzed by using a Shimadzu Model 14-A Gas Chromatograph with a Flame Ionization Detector and a 80/100 Poropak Q column. Based on the results of cyclic voltammetry experiments, the reduction potential of dialkyl carbonate (represented by DMC) was estimated to be around 1.7 V vs. lithium It is appreciated that various modifications to the inventive concepts described herein may be apparent to those of ordinary skill in the art without departing from the spirit and scope of the present invention as defined by the appending claims.

What is claimed is:

1. A method for synthesizing an unsymmetric organic carbonate, comprising the steps of:
   a) providing a first symmetric carbonate having the general formula $R^1OCOOR^1$;
   b) providing a second symmetric carbonate having the general formula $R^2OCOOR^2$, wherein $R^1$ and $R^2$ are selected from the group consisting of saturated alkyl groups, unsaturated alkyl groups and aryl groups; and c) mixing the first and second symmetric carbonates together in the presence of a catalyst selected from the group consisting of a nucleophilic reagent, an electron donating reductant, and mixtures thereof, wherein the electron donating reductant is selected from the group consisting of a metal hydride, an alkyl alkali metal, an aryl alkali metal, an alkali metal, an alkalstod carbon and samarium(II) salt, and mixtures thereof, and wherein the mixture of the first and second symmetric carbonates and the catalyst is devoid of an alcohol.

2. The method of claim 1 including selecting the first and second symmetric carbonates from the group consisting of dimethyl carbonate, diethyl carbonate and dipropyl carbonate.

3. The method of claim 1 wherein the unsymmetric organic carbonate is selected from the group consisting of ethyl methyl carbonate, methyl propyl carbonate and ethyl propyl carbonate.

4. The method of claim 1 including providing the electron donating reductant catalyst having an oxidation potential less than a reduction potential of at least one of the first and second symmetric carbonates.

5. The method of claim 1 including selecting the nucleophilic reagent from the group consisting of metal hydride, alkyl alkali metal, an aryl alkali metal, an alkali metal dialkylamide and an alkali metal alkoxide.

6. The method of claim 1 including providing the first symmetric carbonate and the second symmetric carbonate in a molar ration of about 9:1 to 1:9.

7. The method of claim 1 including performing the synthesis in an inert atmosphere.

8. The method of claim 1 including stirring the first and second symmetric carbonates in the presence of the catalyst.

9. The method of claim 1 including providing the first and second symmetric carbonates in a 1:1 molar ratio.

10. A method for synthesizing an unsymmetric organic carbonate, comprising the steps of:
a) providing a first symmetric carbonate;
b) providing a second symmetric carbonate different than the first symmetric carbonate; and
c) reacting the first and second symmetric carbonates in the presence of either a nucleophilic reagent selected from the group consisting of a metal hydride, an alkyl alkali metal, an aryl alkali metal, an alkali metal dialkylamide and an alkali metal alkoxide, and mixtures thereof, or an electron donating reductant selected from the group consisting of a metal hydride, an alkyl alkali metal, an aryl alkali metal, an alkali metal, an alkalted carbon and samarlaum(II) salt, and mixtures thereof, or a mixture of the nucleophilic reagent and the electron donating reductant, and wherein the mixture of the first and second symmetric carbonates and the catalyst is devoid of an alcohol.

11. The method of claim 10 including selecting the first symmetric carbonate from dimethyl carbonate and dipropyl carbonate, and further including selecting the second symmetric carbonate from diethyl carbonate and dipropyl carbonate, thereby providing the unsymmetric organic carbonate selected from the group consisting of ethyl methyl carbonate, methyl propyl carbonate and ethyl propyl carbonate.

12. The method of claim 10 including providing the first symmetric carbonate and the second symmetric carbonate in a molar ratio of about 9:1 to 1:9.

13. The method of claim 10 including performing the synthesis in an inert atmosphere.

14. The method of claim 10 including stirring the first and second symmetric carbonates in the presence of the catalyst.

15. The method of claim 10 including providing the first and second symmetric carbonates in a 1:1 molar ratio.

16. A method for synthesizing a nonaqueous organic solvent mixture, comprising the steps of:
a) providing a first symmetric carbonate having the general formula $R^1OCOOR^1$;
b) providing a second symmetric carbonate having the general formula $R^2OCOOR^2$, wherein $R^1$ and $R^2$ are selected from the group consisting of saturated alkyl groups, unsaturated alkyl groups and aryl groups; and
c) mixing the first and second symmetric carbonates together in the presence of a catalyst selected from the group consisting of a nucleophilic reagent and an electron donating reductant, and mixtures thereof, wherein the electron donating reductant is selected from the group consisting of a metal hydride, an alkyl alkali metal, an aryl alkali motal, an alkali metal, an alkalated carbon and samariumr(II) salt, and mixtures thereof to thereby provide the solvent mixture consisting of the first symmetric carbonate, the second symmetric carbonate and a product unsymmtetric carbonate, and wherein the mixture of the first and second symmetric carbonates and the catalyst is devoid of an alcohol.

17. The method of claim 16 including providing dimethyl carbonate or dipropyl carbonate as the first symmetric carbonate and either diethyl carbonate or dipropyl carbonate as the second symmetric carbonate so that the unsymmetric carbonate is selected from the group consisting of ethyl methyl carbonate, ethyl propyl carbonate and methyl propyl carbonate.

18. The method of claim 16 including providing the first symmetric carbonate and the second symmetric carbonate in a molar ration of about 9:1 to 1:9.

19. The method of claim 16 including performing the synthesis in an inert atmosphere.

20. The method of claim 16 including stirring the first and second symmetric carbonates in the presence of the catalyst.

21. A method for synthesizing an organic solvent mixture, comprising the steps of:
a) providing a first symmetric carbonate consisting of dimethyl carbonate or dipropyl carbonate;
b) selecting a second symmetric carbonate from diethyl carbonate and dipropyl carbonate; and
c) reacting the first and second symmetric carbonates in the presence of either a nucleophilic reagent selected from the group consisting of a metal hydride, an alkyl alkali metal, an aryl alkali metal, an alkali metal dialkylamide and an alkali metal alkoxide, and mixtures thereof, or an electron donating reductant selected from the group consisting of a metal hydride, an alkyl alkali metal, an aryl alkali metal, an alkali metal, an alkalated carbon and a samarium(II) salt, and mixtures thereof or a mixture of the nucleophilic reagent and the election donating reductant to thereby provide the solvent mixture consisting of the first symmetric carbonate, the second symmetric carbonate and a product unsymmetric carbonate selected from the group consisting of ethyl methyl carbonate, methyl propyl carbonate and ethyl propyl carbonate, and wherein the mixture of the first ad second symmetric, carbonates and the catalyst is devoid of an alcohol.

22. The method of claim 21 including providing the first symmetric carbonate and the second symmetric carbonate in a molar ratio of about 9:1 to 1:9.

23. The method of claim 21 including performing the synthesis in an inert atmosphere.

24. The method of claim 21 including stirring the first and second symmetric carbonates in the presence of the catalyst.

25. A method for synthesizing an unsymmetric organic carbonate, comprising the steps of:
   a) providing a first symmetric carbonate having the general formula $R^1OCOOR^1$;
   b) providing a second symmetric carbonate having the general formula $R^2OCOOR^2$, wherein $R^1$ and $R^2$ are selected from the aroup consisting of saturated alkyl groups, unsaturated alkly groups and aryl groups; and
   c) mixing the first and second symmetric carbonates together in the presence of on electron donating reductant catalyst, wherein the electron donating catalyst has an oxidation potential less than a reduction potential of at least one of the first and second synnmetric carbonates, and wherein the mixture of the first and second symmetric carbonates and the catalyst is devoid of an alcohol.

26. The method of claim 25 wherein the catalyst has a reduction potential below about 1.5 volts versus lithium.

* * * * *